(12) United States Patent
Cho et al.

(10) Patent No.: US 7,074,435 B2
(45) Date of Patent: Jul. 11, 2006

(54) CRUDE DRUG COMPOSITIONS FOR TREATING OR PREVENTING ARTHRITIC DISEASES AND THE PREPARATION PROCESS

(75) Inventors: Byung-Wook Cho, Seoul (KR); Mirim Jin, Seoul (KR); Hyung-Jin Jung, Seoul (KR); Sung-Seup Shin, Seoul (KR); Sunyoung Kim, Seoul (KR); Hyang Jeon, Seoul (KR); Jin-Hwan Oh, Suwon-si (KR); Hae-Kwan Eo, Seoul (KR); Bongcheol Kim, Kyeonggi-do (KR)

(73) Assignee: Pangenomics Co., Ltd. (KR)

( * ) Notice: Subject to any disclaimer, the term of this patent is extended or adjusted under 35 U.S.C. 154(b) by 0 days.

(21) Appl. No.: 10/345,197

(22) Filed: Jan. 16, 2003

(65) Prior Publication Data

US 2003/0143290 A1 Jul. 31, 2003

Related U.S. Application Data

(60) Provisional application No. 60/350,085, filed on Jan. 18, 2002.

(51) Int. Cl.
*A61K 35/78* (2006.01)
(52) U.S. Cl. .................. 424/725; 424/773; 424/775; 424/739
(58) Field of Classification Search ................ 424/725, 424/773, 777
See application file for complete search history.

(56) References Cited

FOREIGN PATENT DOCUMENTS

CN 1171967 A * 2/1998
KR 2000054394 A * 9/2000

OTHER PUBLICATIONS www.holistic-online.com/Herbal-Med/_Herbs/h384.htm.*
www.tcmtreatment.com/herbs.0-qinjiao.htm.*
"The role of cytokines in osteoarthritis pathophysiology"; Julio C. Fernandes, et al., Biorheology 39 (2002) 237-246.
"The molecular mechanism of inhibition of interleukin-1 B-induced cyclooxygenase-2 expression in human synovial cells by Tripterygium wilfordii Hook F extract"; K. Maekawa, et al., Inflamm. res. 48 (1999) 575-581.
"N-Acetylglucosamine Prevents IL-1 B-Mediated Activation of Human Chondrocytes"; Alexander R. Shikhman, et al., The Journal of Immunology, pp. 5155-5160 (2001).
"A New Mechanism of Bone Destruction in Rheumatoid Arthritis: Synovial Fibroblasts Induce Osteoclastogenesis"; Hiroshi Takayanagi, et al., Biochemical and Biophysical Research Communications, 279-286 (1997).

"Adenovirus-Mediated Transfer of Viral IL-10 Gene Inhibits Murine Collagen-Induced Arthritis"; Florence Apparailly, et al., The Journal of Immunology, pp. 5213-5219 (1998).
"Adenoviral Vector-Mediated Overexpression of IL-4 in the Knee Joint of Mice with Collagen-Induced Arthritis Prevents Cartilage Destruction"; Erik Lubberts, et al., The Journal of Immunology, pp. 4546-4556 (1999).
"Prevention of Murine Collagen-Induced Arthritis in the Knee and Ipsilateral Paw By Local Expression of Human Interleukin-1 Receptor Antagonist Protein in the Knee"; Andrew C. Bakker, et al., Arthritis & Rheumatism, vol. 40, No. 5, May 1997, pp. 893-900.
"Angiostatin Gene Transfer as an Effective Treatment Strategy in Murine Collagen-Induced Arthritis"; Jong-Mook Kim, et al., Arthritis & Rheumatism, vol. 46, No. 3, Mar. 2002, pp. 793-801.
Modern Pharmacognosy, Pharmacognosy Research Association, Hakehangsa, pp. 154-158, 1993.
Nature vol. 283, Feb. 14, 1980, pp. 666-668.
"Structure and Function of Synoviocytes"; Dennis A. Carson, et al., pp. 257-267.
"The Encyclopedia of Medicinal Plants", J.H. Park, et al., Shinil Books, pp. 132-134.
"The Encyclopedia of Medicinal Plants", J.H. Park, et al., Shinil Books, pp. 160-161.
"The Encyclopedia of Medicinal Plants", J.H. Park, et al., Shinil Books, pp. 232-233.
"The Encyclopedia of Medicinal Plants", J.H. Park, et al., Shinil Books, pp. 240-242.
"The Encyclopedia of Medicinal Plants", J.H. Park, et al., Shinil Books, pp. 283-285.
"The Encyclopedia of Medicinal Plants", J.H. Park, et al., Shinil Books, pp. 303-305.
"The Encyclopedia of Medicinal Plants", J.H. Park, et al., Shinil Books, pp. 316-317.
"The Encyclopedia of Medicinal Plants", J.H. Park, et al., Shinil Books, pp. 343-345.
"The Encyclopedia of Medicinal Plants", J.H. Park, et al., Shinil Books, pp. 391-393.

(Continued)

Primary Examiner—Susan D. Coe
(74) Attorney, Agent, or Firm—Anderson Kill & Olick, PC

(57) ABSTRACT

The present invention is related to pharmaceutical composition essentially comprising herbal extract of *Chaenomelis Fructus, Achyranthis Radix, Acanthopanax, Phlomidis Radix, Gentianae Radix, Clematidis Radix*, and additionally comprising herbal extract selected from group consisting of *Angelicae Radix, Cnidii Rhizoma, Gastrodiae Rhizoma, Safflower, Cinnamomi Cortex, Job's tear, Aurantii nobilis Pericapium, Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica* according to the need for the prevention and treatment of arthritic diseases and methods of using the above extracts and composition as potent anti-inflammatory and anti-arthritic agents.

5 Claims, 13 Drawing Sheets

OTHER PUBLICATIONS

"The Encyclopedia of Medicinal Plants", J.H. Park, et al., Shinil Books, pp. 409-411.
"The Encyclopedia of Medicinal Plants", J.H. Park, et al., Shinil Books, pp. 418-420.
"The Encyclopedia of Medicinal Plants", J.H. Park, et al., Shinil Books, pp. 424-425.
Herbalogy, Sanitation Press, pp. 169-171.
Herbalogy, Sanitation Press, pp. 309-310.
Herbalogy, Sanitation Press, pp. 311-315.
Herbalogy, Sanitation Press, pp. 320-321.
Herbalogy, Sanitation Press, pp. 347-349.
Herbalogy, Sanitation Press, pp. 379-380.
Herbalogy, Sanitation Press, pp. 479-481.
Herbalogy, Sanitation Press, pp. 501-502.
Herbalogy, Sanitation Press, pp. 504-507.
Herbalogy, Sanitation Press, pp. 602-604.
Herbalogy, Sanitation Press, pp. 662-663.
Herbalogy, Sanitation Press, pp. 684-686.

* cited by examiner

CRUDE DRUG COMPOSITIONS FOR TREATING OR PREVENTING ARTHRITIC DISEASES AND THE PREPARATION PROCESS

CROSS REFERENCE TO RELATED APPLICATION

This application is a continuation patent application of U.S. Provisional Application No. 60/350,085 filed Jan. 18, 2002 abandoned.

DESCRIPTION

1. Field of the Invention

The present invention relates to pharmaceutical composition comprising a herbal extract from various herbs, e.g., *Chaenomelis Fructus, Achyranthis Radix, Acanthopanax, Phlomidis Radix, Gentianae Radix, Clematidis Radix*, based on the known functions of each herb described in various literatures of traditional Chinese and Korean medicine for the prevention and treatment of arthritic diseases and methods of using such extracts and compositions as potent anti-inflammatory and anti-rheumatic agents.

2. Background of the Invention

Arthritis is an autoimmune disease characterized by their symptoms such as pain, swelling and stiffness in the joints. The two major forms of arthritis in mammals are inflammatory arthritis such as rheumatoid arthritis (RA), and osteoarthritis (OA), a progressive, degenerative loss of cartilage often secondary to mechanical stress, aging, dysplastic conditions and/or injury. The symptoms of arthritis generally relate to arthrosis of spine, e.g., hallux rigidus, arthrosis psoriaticum and rheumatic arthritis.

Osteoarthritis produces similar symptoms to rheumatoid arthritis (RA). In particular, although osteoarthritis begins as a degeneration of articular cartilage whereas RA begins as inflammation in the synovium, each process approaches the other as the disease progresses. In osteoarthritis, as cartilage deteriorates and joint congruence is altered, a reactive synovitis often develops. Conversely, as rheumatoid arthritis erodes cartilage, secondary osteoarthritis changes in bone and cartilage development. At the end stages of both osteoarthritis and rheumatoid arthritis, the involved joints appear the same phenomena.

Osteoarthritis usually presents as pain which worsens with exercise or simply an X-ray that clearly shows thinning cartilage. Common joints affected are the knees, hips, spine, finger, base of the thumb and base of the big toe. Osteoarthritis is concerned with destruction of articular cartilage by MMPs (matrix metalloproteinases) which mainly work for cartilage depletion, characterized by degenerative changes in the articular cartilage and an overproduction of inflammatory cytokines, e.g., interleukin-1 (IL-1), tumor necrosis factor-α (TNF-α), thus, it give rise to extremely severe pain in joints, tendons, muscles and ligament (Fernandes J. C., *The role of cytokines in osteoarthritis pathophysiology*, 39, pp237–246, 2002). The primary defect in hyaline cartilage at the articular surface of the joint is an alteration in the ratio of total glucosaminoglycans to that of the collagenin fiber content in the matrix. Paleontologists have found that osteoarthritis exist in almost every vertebrate. Bone underneath the cartilage in joints is called as subchondral bone. This bone nourishes the cartilage with oxygen, water and nutrients conveyed through microscopic channels. This supply route carries chondroprotective agents from the bloodstream to the cartilage.

Rheumatoid arthritis (RA) is a common autoimmune disease characterized by joint swelling, deformation and ultimately, destruction, culminating in severe physical disability. Rheumatic diseases include diseases of the muscles, tendons, joints, bones or sinews, which are generally characterized by inflammation and/or degeneration. Approximately 1~2% of the population suffer from rheumatoid arthritis, which is characterized by an imbalance in the immune system that causes an overproduction of pro-inflammatory cytokines, e.g., TNF-α, IL-1 and a lack of anti-inflammatory cytokines, e.g., IL-10, Il-1. RA is characterized by synovial inflammation, which progresses to cartilage destruction, bone erosion and subsequent joint deformity. During the inflammatory process, polymorphonuclear cells, macrophages and lymphocytes are released. Activated T-lymphocytes produce cytotoxins and pro-inflammatory cytokines, while macrophages stimulate the release of the prostaglandins and cytotoxins. Vasoactive substances (histamine, kinins and prostaglandins) are released at the site of inflammation and cause edema, warmth, erythema and pain associated with inflamed joints.

Among various rheumatic disorders, especially rheumatoid arthritis (RA) belongs to the group of diseases in which the basic pathogenesis is abnormal proliferation of synovial cells accompanied by various immunological disorders caused by internal and external factors and developed to bone and joint erosion.

The main pathology of the affected synovial tissue consists of hyperplasia and subintimal infiltratioin of T and B lymphocytes. Synovial tissue hyperplasia forms in the pannus tissue, while irreversibly destroys the cartilage and bone in the affected joint. RA progression is associated with elevated levels of TNF-α and IL-1β produced by macrophages and dendritic cells, an imbalance of Th1/Th2 and overproduction of antigen specific immunoglobulins. TNF-α and IL-1β directly induce synthesis of proteolytic enzyme such as matrix metalloproteinase (MMPs) that can break down the extracellular matrix macromolecules. Under normal conditions, tissue inhibitors of metalloproteinases (TIMPs) normally bind to MMPs with 1:1 ratio. Imbalance of the ratio of TIMPs to MMPs, which is generally caused by up-regulation of MMPs, results in continued matrix destruction in RA.

Synovial cells play an important role in RA in this way. For example, in the findings of joint lesions with RA, an increase in synovial villi and multi-layerization of synovial cells have been observed and synovial cells are proliferated (Daniel J. McCarty, "Arthritis and Allied Conditions, A Textbook of Rheumatology", 11th Ed.). If a medical substance can inhibit the proliferation of these synovial cells, it is thought to be a therapeutic agent for rheumatic disease. At present, anti-inflammatory agents such as steroid, gold and several cytotoxic agents are used for treating RA, but a specific medical substance, which inhibits proliferation of synovial cells, is not yet known.

Most of the current treatments are directed to the correction of immune aberration that supposedly drives the synovial cell proliferation and cartilage erosion. Present treatment of arthritis includes first line drugs for control of pain and inflammation classified as non-steroidal anti-inflammatory drugs (NSAIDs), e.g., aspirin, ibuprofen, naproxen, methotrexate, etc. Secondary treatments include corticosteroids, slow acting antirheumatic drugs (SAARDs) or disease modifying drugs (DMs), e.g., penicillinamine, cyclophosphamide, gold salts, azothipoprine, levamisole, etc. Glucocorticoides and non-steroidal anti-inflammatory drugs (NSAIDs) are relatively old and conservative treatment for RA. Disease-modifying anti-rheumatic drugs (DMARDs) have been developed. For example, methotrexate (MTX) became a benchmark agent that has efficacy and tolerability in the early phase of RA. Recently, FDA approved leflunomide, an inhibitor of dihydro-orotate dehydrogenase, affects lymphocyte function in vivo and in vitro, although its specific mechanism of action in RA is not yet known. The first groups of biological-response modifiers (BRMs) approved for treatment of RA are the antagonists to TNF-α. They work through binding to its receptor or directly binding to the TNF-α protein. The use of DMARDs has impeded by the potential of long-term side effects and toxicity, while BRM therapy, despite substantial efficacy and clinical improvement, entails high cost and hypersensitivity to the medications and infections due to TNF-α blockage.

Action mechanism of all these drugs is based on suppression of inflammatory reaction, and to our knowledge, no drugs have been developed for cartilage protection. And all of the foregoing drugs have a variety of toxic side effects and most of them are cytotoxic. These drugs have limited advantages and their effects are mainly of short-term duration. The side effects they produce, e.g., gastric erosion, and adverse effects on the kidneys and liver, dictate against their use over extended periods of time. Further, the drugs used at present are costly and have low benefit-risk ratios. There still remains a need for alternative therapies for the management of arthritis which are moderate in cost, safe, efficacious and to eliminate the need for traditional drugs and their associated side effects, particularly over prolonged daily use.

At present, there is a need for the development of new anti-inflammatory and anti-arthritic drugs with reduced side effects and prolonged effects in in vivo experiment. Natural products derived from plants and animals have offered a vast reservoir of materials, which have potential pharmacological effects on humans. Natural products have been the sources of effective drugs and recently there has been an increased interest in the analysis of these natural sources, to find clinically effective materials.

Therefore, the present inventors have endeavored to study the pharmacological effect of *Chaenomelis Fructus, Achyranthis Radix, Acanthopanax, Phlomidis Radix, Gentianae Radix, Clematidis Radix, Angelicae Radix, Cnidii Rhizoma, Gastrodiae Rhizoma, Safflower, Cinnamomi Cortex, Job's tear, Aurantii nobilis Pericapium, Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, based on the known functions of each herb described in various literatures of traditional Chinese and Korean medicine. The features and effects of each herb are as follows.

*Chaenomelis Fructus* is a fruit of *Chaenomeles sinensis* KOENIINE and the same genus plants which belong to Rosaceae and has been used for treating acute gastroenteritis, beriberi, myalgia, arthritis, neuralgia, expectoration, pneumonia, bronchitis (The Encyclopedia of Medicinal Plants, Park J. H. et al., Shinil Books, pp132–134, 2000: Herbalogy, Sanitation press, pp314–315, 1998).

*Achyranthis Radix* is a root of *Achyranthes japonica* NAKAI, *Achyranthes bidentata* BL., *Cyathula officinalis* KUAN and *Cyathula capitata* that belong to Amaranthaceae and has been used for augmenting muscles and bones and treating arthritis (The Encyclopedia of Medicinal Plants, Park J. H. et al., Shinil Books, pp240–242, 2000: Herbalogy, Sanitation press, pp504–507, 1998).

*Acanthopanax* is root bark of *Acanthopanax gracilistylus* W. W. SMITH and the same genus plants, which belong to Araliaceae, and has been used for augmenting muscle, bones and treating edema (The Encyclopedia of Medicinal Plants, Park J. H. et al., Shinil Books, pp283–285, 2000: Herbalogy, Sanitation press, pp320–321, 1998).

*Phlomidis Radix* is a radix of *Phlomis umbrosa* TURCZ. which belongs to Labiatae and has been used for treating bruise, fracture and activating tissue regeneration (The Encyclopedia of Medicinal Plants, Park J. H. et al., Shinil Books, pp232–233, 2000: Herbalogy, Sanitation press, pp662–663, 1998).

*Gentianae Radix* is a radix of *Gentiana macrophylla* PALLAS and the same genus plants, which belong to Gentianceae, and has been used for treating paralysis (The Encyclopedia of Medicinal Plants, Park J. H. et al., Shinil Books, pp391–393, 2000: Herbalogy, Sanitation press, pp311–313, 1998).

*Clematidis Radix* is a radix of *Clematis manshurica* RUPR. and the same genus plants which belong to Ranunculaceae and has been used for treating gout (The Encyclopedia of Medicinal Plants, Park J. H. et al., Shinil Books, pp303–305, 2000: Herbalogy, Sanitation press, pp309–310, 1998).

*Angelicae Radix* is a radix of *Angelica gigas* NAKAI, *Angelica sinensis* DEILS and *Angelica acutiloba* KITAGAWA that belong to Umbelliferae and has been used for puerperium disease, hematoporia, headache and augmenting and protecting blood stream (The Encyclopedia of Medicinal Plants, Park J. H. et al., Shinil Books, pp409–411, 2000: Herbalogy, Sanitation press, pp684–686, 1998).

*Cnidii Rhizoma* is a rhizoma of *Cnidium officinale* MAKINO, *Ligusticum chuanxiong* HORT, *Ligusticum wallichii* FRANCH var. *officinale* YOOK and *Angelica genuflexa* MUTT which belong to Umbelliferae and has been used for treating hematoporia, headache, obstetrics and gynopathic disease (The Encyclopedia of Medicinal Plants, Park J. H. et al., Shinil Books, pp418–420, 2000: Herbalogy, Sanitation press, pp479–481, 1998).

*Gastrodiae Rhizoma* is a dried rhizoma bark of *Gastrodia elata* BLUME that belongs to Orchidaceae and has been used for treating headache and dizziness (The Encyclopedia of Medicinal Plants, Park J. H. et al., Shinil Books, pp424–425, 2000: Herbalogy, Sanitation press, pp602–604, 1998).

*Safflower* is dried flower of *Carthamus tinctorius* L. which belongs to Compositae has been used for treating gynopathic disease, leukorrhea, climacteric disease (The Encyclopedia of Medicinal Plants, Park J. H. et al., Shinil Books, pp343–345, 2000: Herbalogy, Sanitation press, pp501–502, 1998).

*Cinnamomi Cortex* is stem bark of *Cinnamomum cassia* BLUME which belongs to Lauraceae has been used for mixing with other herbs for treating cold, ataralgesia (Modern Pharmacognosy, Pharmacognosy Research Association, Hakchangsa, pp154–158, 1993).

*Ledebouriellae Radix* is a root of *Ledebouriella seseloides* WOLF. which belongs to Umbelliferae and has been used for treating cold, headache, arthritis, tetanus (The Encyclopedia of Medicinal Plants, Park J. H. et al., Shinil Books, pp160–161, 2000: Herbalogy, Sanitation press, pp169–171, 1998).

Job's tear is a seed removed seed coat of *Coix lacryma-jobi* L. var. *mayuen* STAPF which belongs to Gramineae and has been used for treating catharsis, rhinalgia (The Encyclopedia of Medicinal Plants, Park J. H. et al., Shinil Books, pp316–319, 2000: Herbalogy, Sanitation press, pp347–349, 1998).

Additionally, it is well known that *Atractylodes Rhizoma, Lonicera japonica, Akebiae caulis, Caragana chamlagu, Licorice root, Notopterygium incisum, Persicae semen, Eucommia ulmoides, Torilis japonica* has been used for augmenting muscles, bones and eliminating gout.

*Chaenomelis Fructus, Achyranthis Radix, Cnidii Rhizoma* and *Cinnamomi Cortex* are known for their function in keeping or assisting blood circulation. *Angelica Radix* and *Gastrodiae Rhizoma* were chosen for their activities in tonifying the blood. *Ledebouriellae Radix* was described to catalyze the function of other reagents. *Gentianae Radix* and *Acanthopanax root-bark* were reported to assist with the functions of both muscle and bone, while *Clematidis Radix* and *Phlomidis Radix* have been used for potentiation of cartilage and regeneration of damaged tissue. All the raw materials used for the complex herbal formulation are listed in the Korean Pharmacopoeia or the Korean Herbal Pharmacopoeia and complex herbal composition has been used by a selective group of oriental medicine physicians in Korea.

Therefore, the present inventors have endeavored to study the pharmacological effect of above mentioned herbal extract and its composition on inflammatory and arthritic diseases, and have found that the complex herbal extract and its composition from above herbs are effective in treating and preventing arthritic and inflammatory diseases.

SUMMARY OF THE INVENTION

According to one aspect, the present invention provides a complex herbal composition essentially comprising herbal extracts of *Chaenomelis Fructus, Achyranthis Radix, Acanthopanax, Phlomidis Radix, Gentianae Radix, Clematidis Radix* for preventing and treating inflammatory and arthritic diseases.

The present invention also provides a complex herbal composition additionally comprising herbal extract selected from the group consisting of *Angelicae radix, Cnidii Rhizoma, Gastrodiae Rhizoma, Safflower, Cinnamomi Cortex, Job's tear, Aurantii nobilis* Pericapium, *Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, besides above-mentioned essential complex herbs for preventing and treating inflammatory and arthritic diseases.

The present invention also provides pharmaceutical compositions comprising the above-mentioned complex herbal composition as an active ingredient in an amount effective to preventing and treating inflammatory and arthritic diseases, together with a pharmaceutically acceptable carrier.

The present invention also provides a method for treating inflammatory or arthritic diseases, comprising administrating the above mentioned extract.

The present invention also provides a use of the above-mentioned extract as an active ingredient in medicaments for treating inflammatory or arthritic diseases.

The present invention also provides a health food comprising the above mentioned complex herbal composition as an active ingredient in an amount effective to preventing inflammatory and arthritic diseases, together with a sitologically acceptable additive.

The present invention still provides processes for preparing the above-mentioned complex herbal composition.

BRIEF DESCRIPTION OF THE DRAWINGS

In order that the invention may be better understood preferred embodiments will now be described by way of example only with reference to the accompanying drawings wherein.

DETAILED DESCRIPTION

Figure 1:
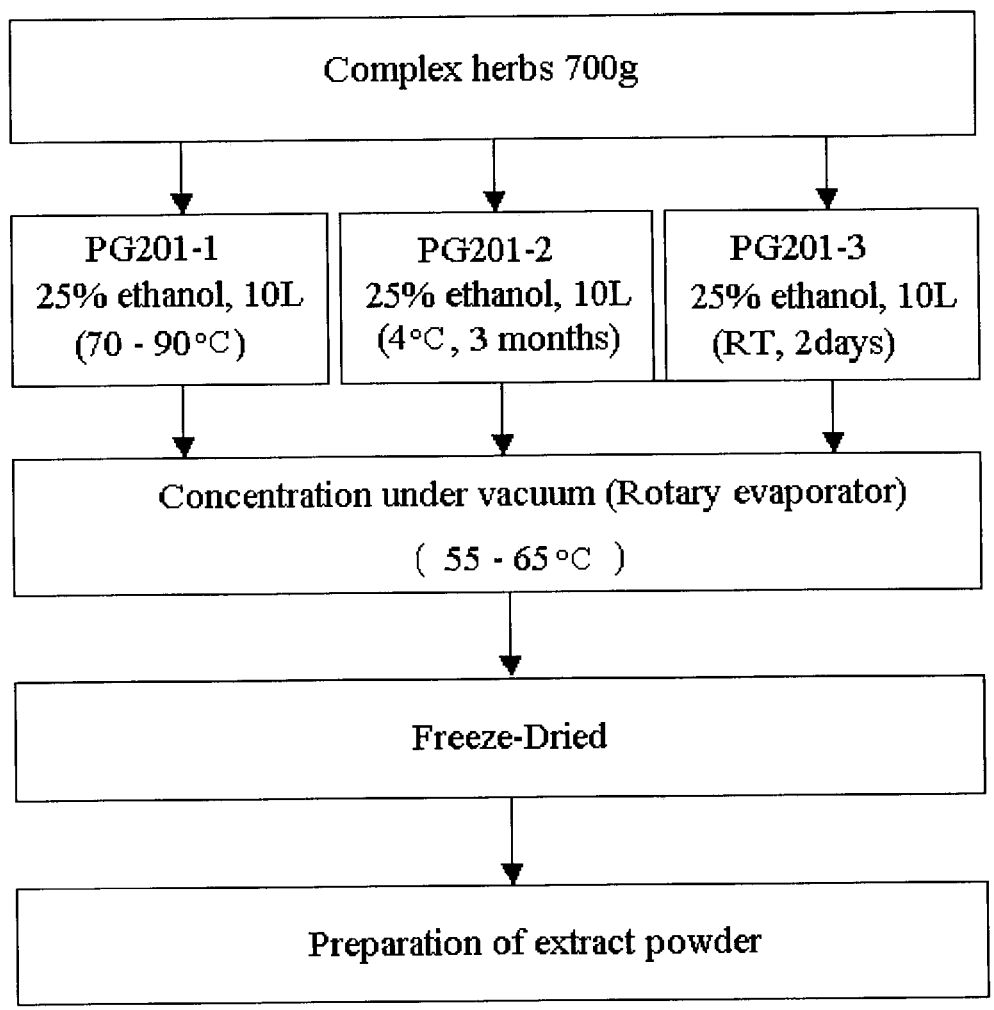
FIG. 1 presents the flow chart of the PG201-1, PG201-2 and PG201-3 in the present invention.

Accordingly, it is an object of the present invention to provide a complex herbal composition essentially comprising a complex herbal extract of *Chaenomelis Fructus, Achyranthis Radix, Acanthopanax, Phlomidis Radix, Gentianae Radix, Clematidis Radix* for preventing and treating inflammatory and arthritic diseases.

Above described *Chaenomelis Fructus* comprises a fruit of the one selected from *Chaenomeles sinensis* KOENHNE and the same genus plants such as *Chaenomeles speciosa* NAKAI, *Chaenomeles lagenaria* KOIDZ, *Chaenomeles japonica* SPACH and *Chaenomeles thibetica*.

Above described *Achyranthis Radix* comprises a root of the one selected from *Achyranthes japonica* NAKAI, *Achyranthes bidentata* BL., *Cyathula officinalis* KUAN and *Cyathula capitata*.

Above described *Acanthopanax* comprises fruit, leaf, stem and root of the one selected from *Acanthopanax gracilistylus* W. W. SMITH and the same genus plants such as *Acanthopanax sessilflorus* SEEM., *Acanthopanax koreannum* NAKAI, *Acanthopanax rufinerve* NAKAI, *Acanthopanax senticosus* HARMS, *Acanthopanax senticosus* var. *koreanus* NAKAI, *Acanthopanax seoulense* NAKAI and *Acanthopanax sieboldianum* MAKINO.

Above described *Phlomidis Radix* comprises a radix of the one selected from *Phlomis umbrosa* TURCZ., *Phlomis koraiensis* NAKAI, *Dipsacus japonicus* MIQ., *Dipsacus asper, Dipsacus chinensis* and *Dipsacus fullonum*.

Above described *Gentianae Radix* comprises a radix of the one selected from *Gentiana macrophylla* PALLAS and the same genus plants such as *Gentiana scabra* BUNGE var. *buergeri* MAX., *Gentiana manshurica, Gentiana lutea*.

Above described *Clematidis Radix* comprises a radix of the one selected from *Clematis manshurica* RUPR. and the same genus plants such as *Clematis chiisanensis, Clematis triflora* CHUNG and *Clematis armandii*.

It is another object of the present invention to provide a complex herbal composition additionally comprising herbal extract selected from the group consisting of *Angelicae Radix, Cnidii Rhizoma, Gastrodiae Rhizoma, Safflower, Cinnamomi Cortex, Job's tear, Aurantii nobilis* Pericapium, *Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, besides above mentioned essential complex herbs, for preventing and treating inflammatory and arthritic diseases.

Above described *Cnidii Rhizoma* comprises a rhizoma of the one selected from *Cnidium officinale* MAKINO, *Ligusticum chuanxiong* HORT, *Ligusticum wallichii* FRANCH var. *officinale* YOOK, *Ligusticum monnieri, Ligusticum japonicum* and *Ligusticum lucidum*.

Above described *Safflower* is dried flower and its seed of *Carthamus tinctorius* L.

Above described *Ledebouriellae Radix* comprises a root of the one selected from *Ledebouriella seseloides* WOLF., *Peucedanum japonicum* THUNB., *Peucedanum decursivum* MAXIM. and *Peucedanum ostruthium*.

In accordance with one aspect of the present invention, there provided a pharmaceutical composition essentially comprising a complex herbal extract of *Chaenomelis Fructus, Achyranthis Radix, Phlomidis Radix, Gentianae Radix, Clematidis Radix* and a pharmaceutically acceptable carrier thereof as an active ingredient for treating and preventing inflammatory and arthritic diseases.

It is another object of the present invention to provide a pharmaceutical composition additionally comprising complex herbal extract selected from the group consisting of *Angelicae radix, Cnidii Rhizoma, Gastrodiae Rhizoma, Safflower, Cinnamomi Cortex, Job's tear, Aurantii nobilis* Pericapium, *Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, besides above essential complex herbs and a pharmaceutically acceptable carrier thereof as an active ingredient for preventing and treating arthritic diseases.

Further, it is another object of the present invention to provide a pharmaceutical composition containing *Chaenomelis Fructus, Achyranthis Radix, Acanthopanax, Phlomidis Radix, Gentianae Radix* and *Clematidis Radix*, preferably with a ratio of. 1:0.5~2:0.5~2:0.5~2:0.5~2:0.5~2.

The above herbs include their same genus plants which would be apparent to those skilled in the art and can be substituted for the prevention and treatment of arthritic diseases.

The pharmaceutical composition for treating arthritic diseases could contain about 0.01 to 95 w/w %, preferably 0.5 to 80 w/w % of the above herbal extract of present invention based on the total weight of the composition.

An inventive extract may be prepared in accordance with the following preferred embodiment.

For the present invention, above extract can be prepared by following procedure; herbs, i.e., *Chaenomelis Fructus, Achyranthis Radix, Acanthopanax, Phlomidis Radix, Gentianae Radix, Clematidis Radix* are washed, dried and cut into small pieces. Each pieces of above herbs is mixed with preferably the ratio (w/w) of 1:1:1:0.5~2:0.5~2:0.5~2, otherwise, additional herbs such as *Angelicae Radix, Cnidii Rhizoma, Gastrodiae Rhizoma, Safflower, Cinnamomi Cortex, Ledebouriellae Radix, Lonicera japonica, Akebiae caulis, Caragana chamlagu, Licorice root, Notopterygium incisum, Persicae semen, Eucommia ulmoides, Atractylodes Rhizoma* and *Torilis japonica* can be co-mixed at the stage. The herbs are mixed with 5 to 20-fold, preferably, 10 to 15-fold volume of distilled water, alcohols such as methanol, ethanol and the like, or the mixtures thereof, preferably, the mixture of ethanol and water, more preferably with the ratio of 1:1 to 1:9; and is enfleuraged at the temperature ranging from 0 to room temperature, preferably from 4 to 6° C., for the period ranging from 12 hours to 5 months, preferably 1 to 3 months or heated at the temperature ranging from 80 to 100° C., preferably above 90° C., for the period ranging from 1 to 24 hours, preferably 3 to 5 hours with 2 to 5 times, by sonication, reflux or conventional extraction to obtain an aqueous complex herbal extract. The herbal extract is filtered and concentrated at 40 to 80° C. under reduced pressure. The extract is concentrated by azotropic distillation with volume of 10 to 60-fold water, 1 to 5 times and then dried by freeze drying or vacuum drying to obtain a complex herbal extract powder.

It is another object of the present invention to provide a process for preparing complex herbal composition described above.

It is another object of the present invention to provide a complex herbal composition comprising *Chaenomelis Fructus, Achyranthis Radix, Acanthopanax, Phlomidis Radix, Gentianae Radix* and *Clematidis Radix* with the ratio of 1:0.5~2:0.5~2:0.5~2:0.5~2:0.5~2 thereof and additional herbs having appropriate ratio could be mixed for need.

In accordance with the present invention, there provided a complex herbal composition which can add or remove properly another herbs and increase or decrease composition ratio of herbs for keeping an effective therapeutic activity against arthritic diseases.

The complex herbal composition of the present invention has potent anti-inflammatory activity and the pharmaceutical composition of the present invention thus may be employed for acute, chronic rheumatoid, atrophic arthritis, chronic inflammatory arthritis, arthritis deformans, infectious arthritis, menopausal arthritis, arthritis mutilans, hypertrophic arthritis, suppurative arthritis, tuberculos arthritis or degenerative arthritis.

In accordance with another aspect of the present invention, there is also provided a use of the complex herbal composition comprising above mentioned complex herbal extract in the manufacture of a medicament for preventing or treating arthritic diseases In accordance with another aspect of the present invention, there is also provided a method of treating of arthritis in a mammal comprising administering to said mammal an effective amount of a complex herbal composition and pharmaceutically acceptable carrier thereof.

It is another of the present invention to provide a method of enhancing cartilage formation in a mammal comprising administering to said mammal an effective amount of a complex herbal composition and pharmaceutically acceptable carrier thereof.

It is another of the present invention to provide a method for alleviating acute, chronic rheumatoid, atrophic arthritis, chronic inflammatory arthritis, arthritis deformans, infectious arthritis, menopausal arthritis, arthritis mutilans, hypertrophic arthritis, suppurative arthritis, tuberculos arthritis or degenerative arthritis in a mammal comprising administering to said mammal an effective amount of a complex herbal composition and pharmaceutically acceptable carrier thereof.

It is another of the present invention to provide an antiphlogistic and analgesic drug comprising the above complex herbal composition as an active ingredient in an amount effective to preventing and treating inflammatory and arthritic diseases.

It is another of the present invention to provide a treating method by administrating a pharmaceutical composition comprising above complex herbal composition to humans and the other mammals for inflammatory and arthritic diseases.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The complex herbal composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing complex herbal composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The complex herbal composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 0.01–10 g/kg, preferably, 1 to 5 g/kg by weight/day of the inventive extract or compounds of the present invention. The dose may be administered in a single or multiple doses per day. In terms of composition, the complex herbal composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The present inventors demonstrated that the inhibitory and anti-inflammatory effects of complex herbal composition is potent by accomplishing in vivo experiments, e.g., collagen-induced arthritis (CIA) in mice model test, inhibition test of cytokines such as TNF-α, IL-1β in the paws, protection effect against cartilage destruction by affecting the level of MMP and TIMP, human study, therefore, it is confirmed that above described complex herbal composition is very useful in the prevention or treatment of inflammatory and arthritic disease.

The complex herbal composition of the present invention provides prevention for cartilage destruction, most important symptom in the arthritic symptoms, thus it is very useful for patients suffering with arthritis, e.g., cartilage destruction.

Accordingly, it is another object of the present invention to provide a health food essentially comprising a complex herbal extract of *Chaenomelis Fructus, Achyranthis Radix, Acanthopanax, Phlomidis Radix, Gentianae Radix* and *Clematidis Radix* and a sitologically acceptable additive to prevent arthritic diseases, e.g., rheumatic arthritis.

It is another object of the present invention to provide a health food additionally comprising complex herbal extract selected from the group consisting of *Angelicae radix, Cnidii Rhizoma, Gastrodiae Rhizoma, Safflower, Cinnamomi Cortex, Job's tear, Aurantii nobilis* Pericapium, *Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, besides above essential complex herbs and a sitologically additive to prevent arthritic diseases.

The health food composition for preventing arthritic diseases could contain about 0.01 to 95 w/w %, preferably 0.5 to 80 w/w % of the above herbal extract of present invention based on the total weight of the composition.

Above described the complex herbal composition therein can be added to food, additive or beverage for prevention of arthritic diseases. For the purpose of preventing arthritic diseases, wherein, the amount of above described extract or compound in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described extract or compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/W % per 100 w/w % present composition.

Examples of addable food comprising aforementioned extract therein are various food, beverage, gum, vitamin complex, health improving food and the like.

In accordance with another aspect of the present invention, there are provided a feed essentially comprising a complex herbal extract of *Chaenomelis Fructus, Achyranthis Radix, Acanthopanax, Phlomidis Radix, Gentianae Radix* and *Clematidis Radix* as an active ingredient for the livestock, to prevent arthritic diseases.

It is another object of the present invention to provide a feed additionally comprising complex herbal extract selected from the group consisting of *Angelicae radix, Cnidii Rhizoma, Gastrodiae Rhizoma, Safflower, Cinnamomi Cortex, Job's tear, Aurantii nobilis* Pericapium, *Ledebouriellae Radix, Lonicera japonica, Akebiae caulis, Caragana chamlagu, Licorice root, Notopterygium incisum, Persicae semen, Eucommia ulmoides, Atractylodes Rhizoma, Torilis japonica*, besides above essential complex herbs as an active ingredient for the livestock, to prevent arthritic diseases.

Inventive feed additive can be added with the range from 0.01 to 95w/w %, preferably 0.5 to 80w/w % of the above herbal extract in feed to treat and prevent arthritic diseases of the livestock.

In accordance with another aspect of the present invention, there is also provided an use of the feed comprising above complex herbal extract for manufacture of the livestock feed employed for preventing or treating arthritic diseases.

In accordance with another aspect of the present invention, there is also provided a method of preventing or treating arthritic diseases on livestock, wherein the method comprises administering a therapeutically effective amount of the complex herbal composition and acceptable carrier thereof.

In accordance with another aspect of the present invention, there are provided a method of preventing or treating for feed and a feed additive comprising the above-mentioned composition to treat and prevent arthritic diseases of the livestock.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

Example 1

Preparation of PG201-1

1-1. Extraction by Using Water Solvent

All herbs used were purchased from a market specializing in herbs (Kyungdong herb market, Seoul, Korea). Each herb, of which moisture was less than 10% of weight, was air-dried and mixed with 80 g of each *Chaenomelis Fructus, Achyranthis Radix, Acanthopanax, Cinnamomi Cortex* and then added with 50 g of each *Gentianae Radix, Clematidis Radix, Angelicae Radix, Cnidii Rhizoma, Gastrodiae Rhizoma, Safflower* and 40 g of each *Phlomidis Radix, Ledebouriellae Radix* and minced by a grinder (Rong Tong Iron Works, Taiwan). The mixed herb was added with 10 l of 25% alcohol, stirred, refluxed 3 times at 90~95° C. for 3 hours and filtered. The filtrate was concentrated at 55~65° C., freeze-dried to obtain 70 g of complex herbal extract powder (FIG. 1).

1-2. Extraction by Using Water-ethanol Solvent.

The same herbs in the above Example 1-1 were added with 10 l of 25% alcohol, stirred, refluxed 3 times at 90~95° C. and filtered. The filtrate was concentrated at 55~65° C., freeze-dried to obtain 70 g of complex herbal extract powder (PG201-1) and used as a test sample (FIG. 1).

Example 2

Preparation of PG201-2

The same herbs in the above Example 1-1 were added with 10 l of 25% alcohol and stirred. The mixture solution was extracted at 4° C. for each of 3 months, 6 months and 12 months and filtered, respectively. The filtrate was concentrated at 55~65° C. and freeze-dried to obtain 70 g of complex herbal extract powder (PG201-2) and used as test sample (FIG. 1).

Example 3

Preparation of PG201-3

The herbs, e.g., *Chaenomelis Fructus, Achyranthis Radix, Acanthopanax, Phlomidis Radix, Gentianae Radix* and *Clematidis Radix* were used. 80 g of each herbs was mixed, added with 10 l of 25% alcohol, extracted by stirring at room temperature for 2 days and filtered. The filtrate was concentrated at 55~65° C., freeze-dried to obtain 45 g of complex herbal extract power (PG201-3) and used as test sample (FIG. 1).

Reference Example 1

Comparison of Extraction Method and Herbal Yield of its Level

The complex herbs were mixed and extracted 3 times by reflux and enfleurage, respectively. The result was expressed by percentage (%) of each stage yield to total yield in accordance with the number of extraction and extraction period (Table 1).

TABLE 1

Comparison of extract yield by the condition of extraction

| Extraction method | | No. of Extraction | | |
|---|---|---|---|---|
| | | Primary | Secondary | Third |
| Extraction of Example 1 (Reflux) | Only water | 65% | 25% | 10% |
| | Mixture solvent | 70% | 25% | 5% |
| Extraction of Example 2 (Enfleurage) | 3 months | 65% | 25% | 10% |
| | 6 months | 70% | 25% | 5% |
| | 12 months | 70% | 25% | 5% |

As can be seen in Table 1, the test result demonstrated that all the extraction method of Example 1 and 2 are accomplished with above 90% yield by secondary extraction, therefore, it is confirmed that the third extraction is unnecessary and uneconomic.

Experiment Example 1

Collagen-induced Arthritis (CIA) in Mice Model Test

Method

In order to confirm the therapeutic effect of the PG201-1 and PG201-2 obtained in above the Example 1 to Example 2 on rheumatic arthritis, the experiment was performed with the procedure described in the literature (Courtenay J. S., et al., *Nature*, 283, pp666–668, 1980; Kim J. M., et al., *Arthritis Rheum.*, 46, pp793–801, 2002).

Preparation of CIA Model

Figure 2:
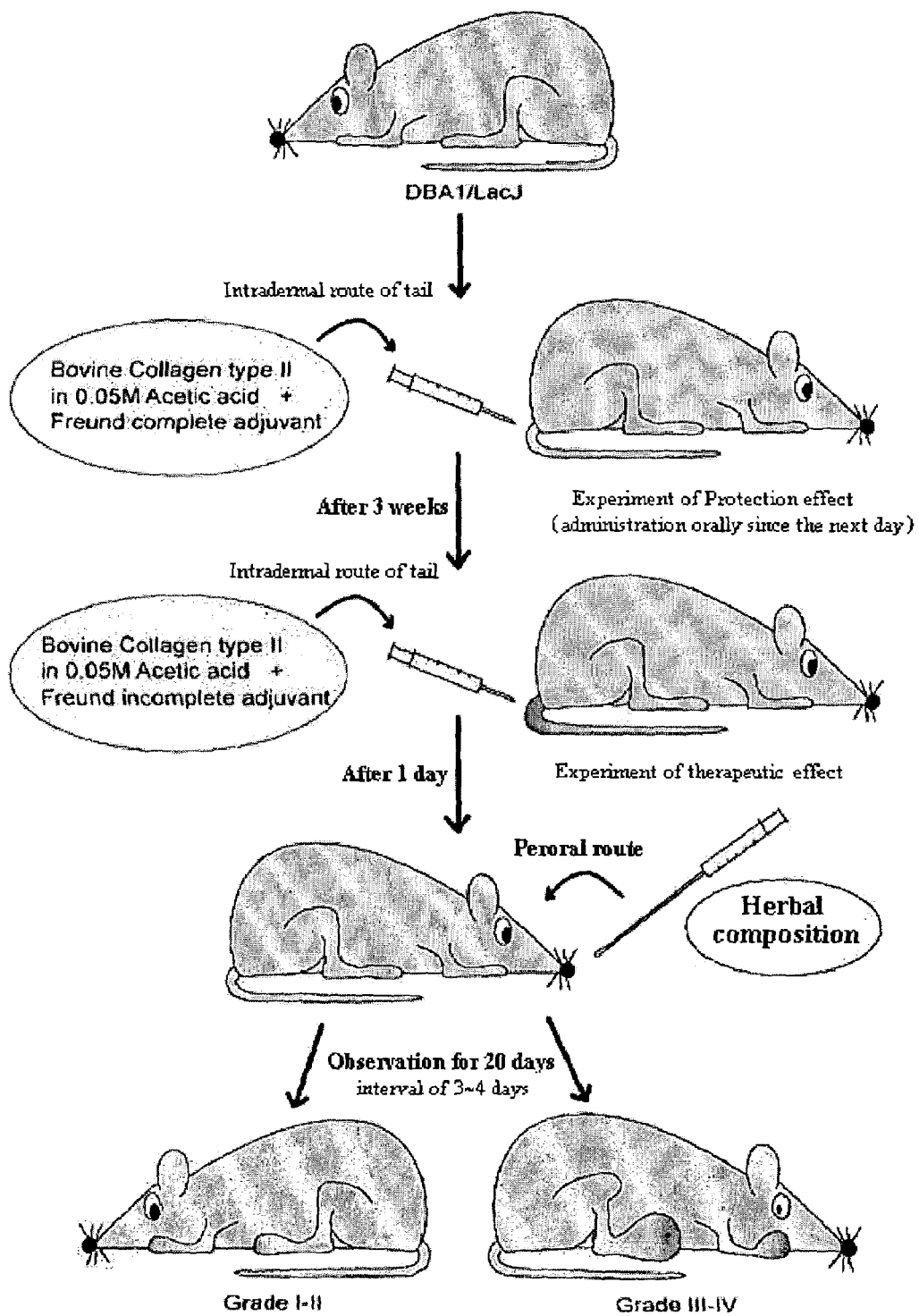
FIG. 2 presents the flow chart of the experiment of Collagen-induced arthritis (CIA) in mice and preventive and therapeutic process for induced arthritis therefrom.

Inbred male DBA/1 mice (Jackson Laboratory, Maine, USA), aged 9~10 weeks, were used and immunized intradermally at the base of the tail with 100 μg bovine type II collagen (Chondrex, Wash. USA) emulsified in Freund's complete adjuvant (Gibco BRL, NY, USA) and then, on day 21 after initial immunization, all the mice were boosted with an intradermal injection of 100 μg type II collagen emulsified in Freund's incomplete adjuvant (Gibco BRL, NY, USA). Gradual arthritic symptom normally appears approximately 1~2 weeks after secondary immunization (FIG. 2).

Preventive Effect of Arthritis After First Immunization

Figure 3:
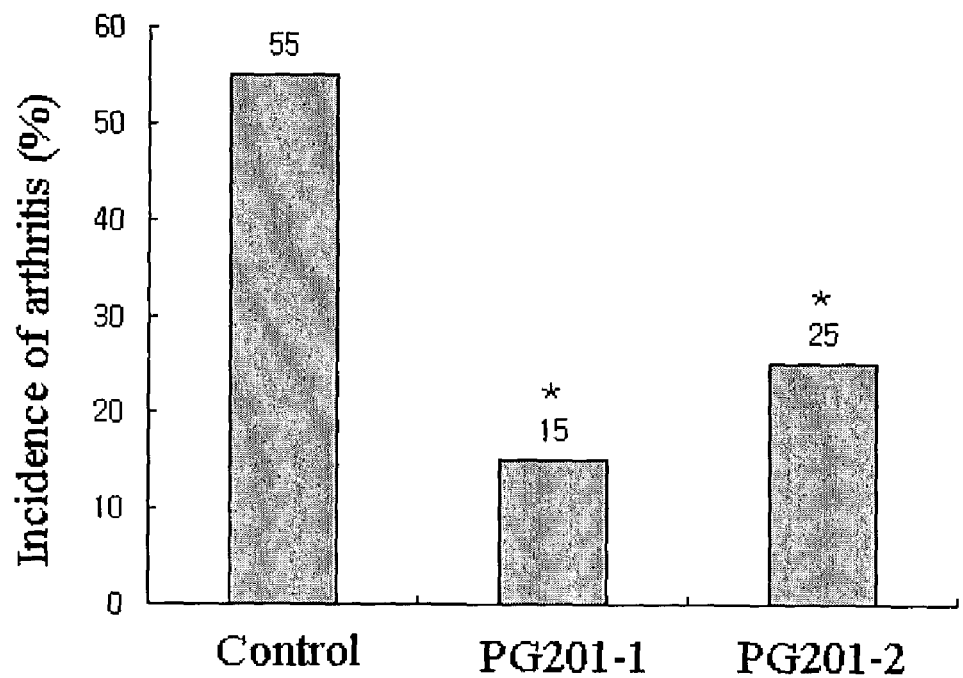
FIG. 3 presents protection of an incidence of arthritis by administration of PG201-1 and PG201-2 in CIA.

Test samples were administrated to the above mice by using oral kit the next day after the first immunization where each group consisted of 10 mice. Test sample solution containing PG201-1 in Example 1 was prepared at the concentration of 100 mg/ml by dissolving the sample in sterilized water and 100 μl of the solution was administrated to one group. Test sample solution containing PG201-2 at the concentration of 100 mg/ml by dissolving the sample in 30% ethanol and 100 μl of the solution was administrated to other group. Negative control group was administrated orally with distilled water and other control group was administrated orally with 30% alcohol. CIA progressions were evaluated by macroscopic symptoms such as joint swelling; histologic symptoms such as hyperplasia of synovial fibroblasts, cartilage damage; and molecular biologic symptoms such as cytokine expression level relating to cartilage destruction and protection. Arthritis was considered to be present if the index grade of arthritis showed above 2. An incidence rate of arthritis was transformed into percentage (FIG. 3).

Preventive Effect of Arthritis After Secondary Immunization

Figure 4A:
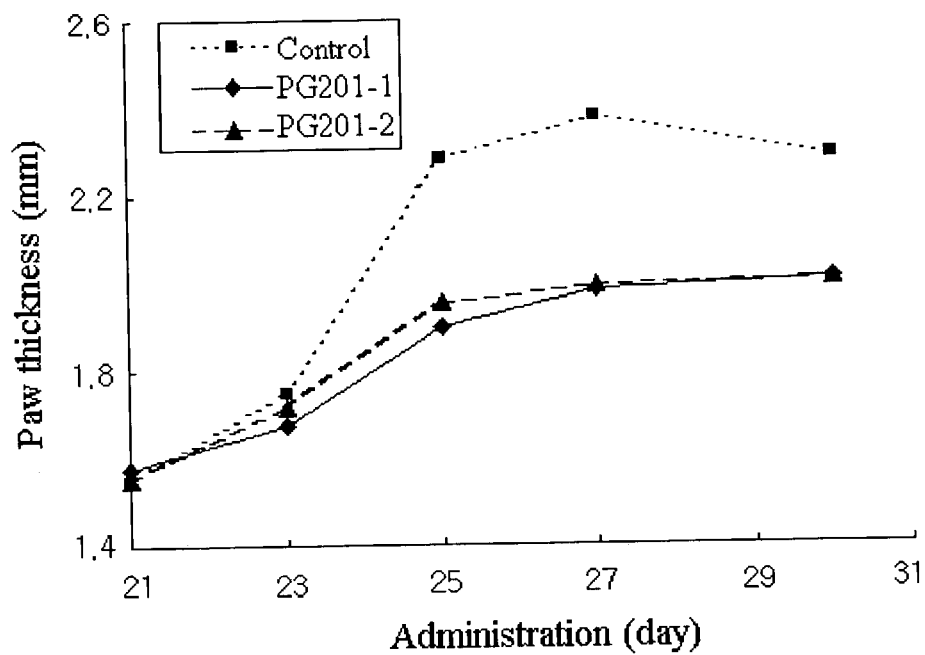
FIG. 4a represents therapeutic effect for paw thickness by administrating of PG201-1 and PG201-2 in CIA.
Figure 4B:
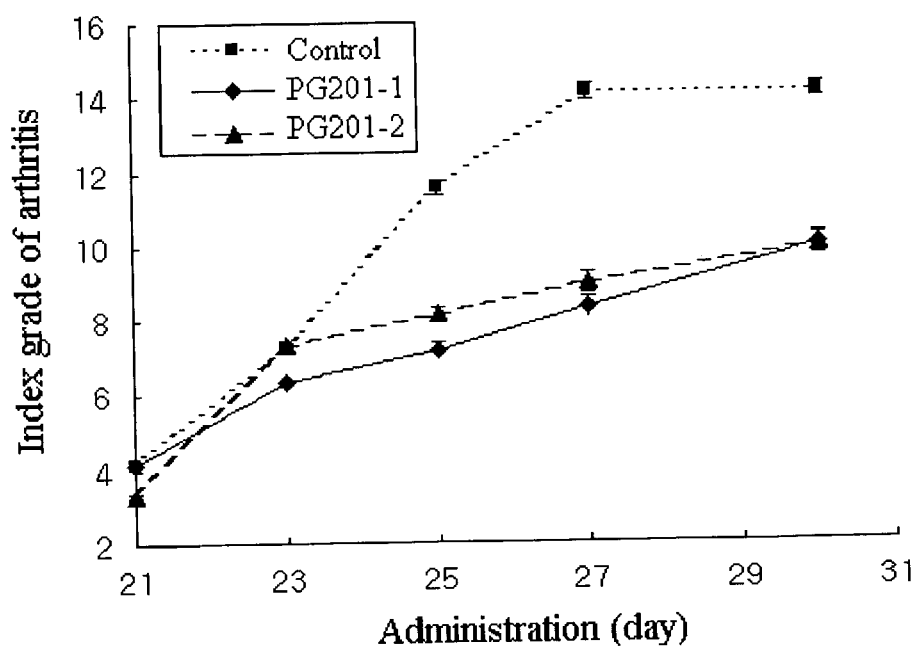
FIG. 4b presents therapeutic effect for index grade of arthritis by administrating PG201-1 and PG201-2 in CIA.
Figure 5A:
FIG. 5a shows hyperplasia level of synovial fibroblasts of the control group in knee joint of CIA mice.
Figure 5B:
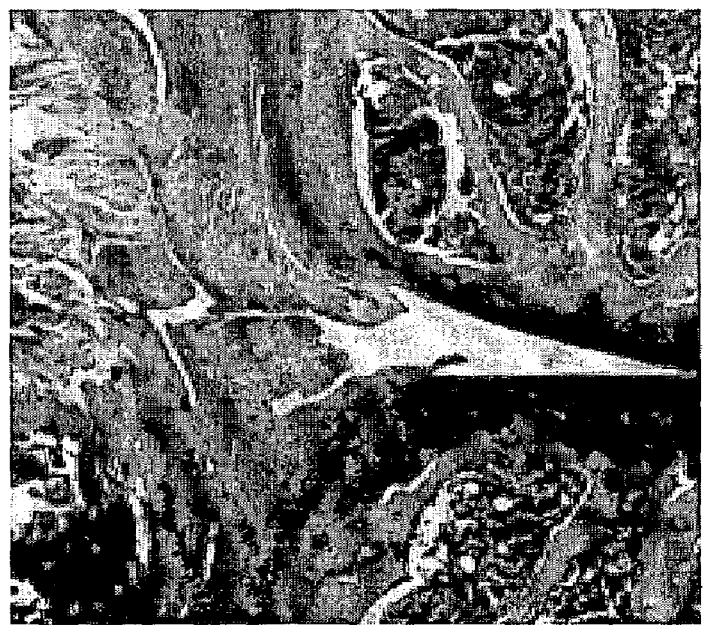
FIG. 5b presents cartilage depletion level of the control group in knee joint of CIA mice.
Figure 5C:
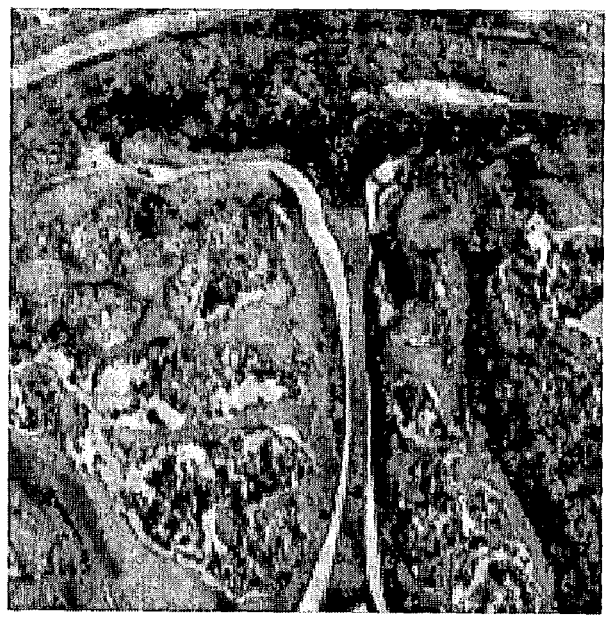
FIG. 5c represents hyperplasia level of synovial fibroblasts of the PG201-1 group in knee joint of CIA mice.
Figure 5D:
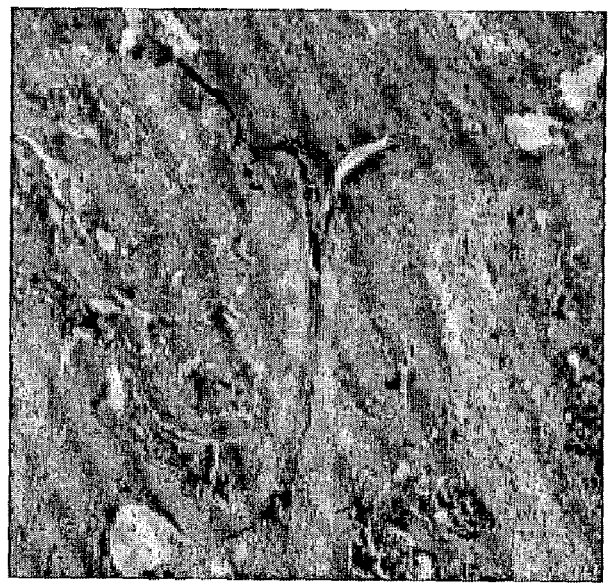
FIG. 5d presents cartilage depletion level of the PG201-1 group in knee joint of CIA mice.
Figure 5E:
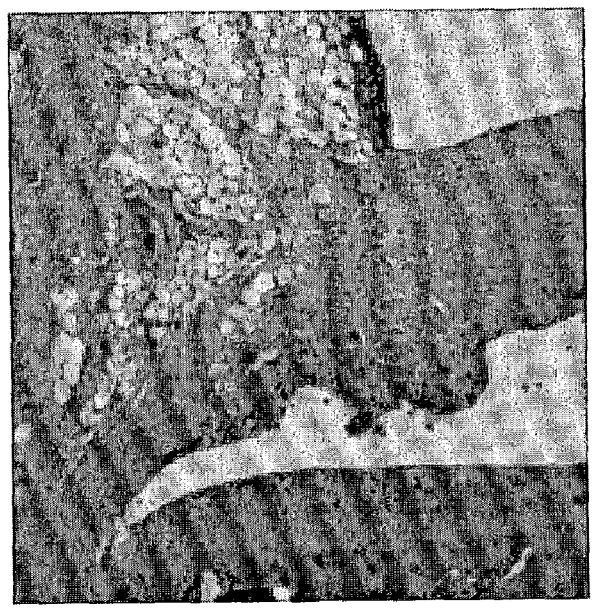
FIG. 5e represents hyperplasia level of synovial fibroblasts of the PG201-2 group in knee joint of CIA mice.
Figure 5F:
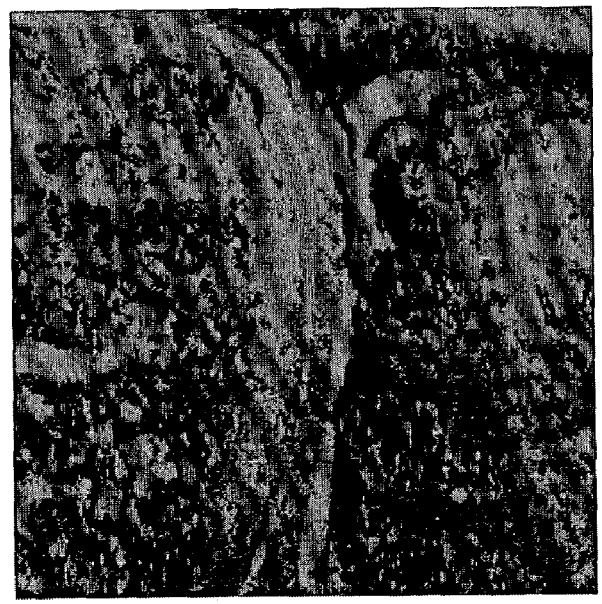
FIG. 5f shows cartilage depletion level of the PG201-2 group in knee joint of CIA mice.

The mice were administrated with the sample by using oral kit the next day after secondary immunization where each group consisted of 10 mice. Test sample solution containing PG201-1 in Example 1 was prepared at the concentration of 100 mg/ml by dissolving the sample in sterilized water and 100 μl of the solution was administrated to one group. Test sample solution containing PG201-2 at the concentration of 100 mg/ml by dissolving the sample in 30% ethanol and 100 μl of the solution was administrated to other group. Negative control group was administrated orally with distilled water and other control group was administrated orally with 30% alcohol. CIA progressions were evaluated by macroscopic symptoms such as joint swelling; histologic symptoms such as hyperplasia of synovial fibroblasts, cartilage depletion; and molecular biologic symptoms such as cartilage destruction, cytokine level and the like. Arthritis was considered to be present at the basis of paw thickness of joint and index grade of arthritis (FIG. 4a and FIG. 4b).

Measurement for Severity of Arthritis

Main histopathological symptoms of rheumatic arthritis were summarized by hyperplasia of synovial fibroblasts and irreversible destruction of cartilage system therefrom, which is effective in histological analysis. In order to measure or determine arthritis severity, the experiment was performed with histological analysis by separating knee joint of the control group, PG201-1 and PG201-2 group, respectively.

Mice was sacrificed by cervical dislocation, thereafter, knee joints were dissected, fixed in 10% phosphate-buffered formalin for 2 days, decalcified in 10% EDTA for 7 days, and then embedded in paraffin. Standard frontal sections having 7 μm diameter were prepared, stained with either hematoxylin/eosin or safranin O/fast green staining agent (Bakker A. C. et al., *Arthritis and Rheumatism*, 40, pp893–900, 1997; Apparailly Florence et al., *J. Immunol.*, 160, pp5213–5220, 1998).

Histopathological changes were scored by using the following parameters as previously described.

Hyperplasia of synovial fibroblasts was visualized by diminished hematoxylin/eosin staining and the severity of them was scored arbitrarily as 0 when normal; 1 when slight inflammation and hyperplasia of synovial fibroblasts; 2 when formation of pannus and extreme hyperplasia of synovial fibroblasts according to the degree of hyperplasia. Arthritis was considered to be present if the degree of hyperplasia of synovial fibroblasts showed above 2, which is described in the literature (Apparailly Florence et al., *J. Immunol.*, 160, p5213–5220, 1998; Lubberts Erik et al., *J. Immunol.*, 163, pp4546–4556, 1999).

Depletion of articular cartilage was visualized by diminished safranin O-staining of proteoglycan matrix and scored arbitrarily as 0 when normal; 1 when vacuolation of chondrocyte tissue or disappearance of proteoglycan; 2 when cartilage erosion added to the symptom in score 1; 3 when above two point of cartilage erosion and destruction of subcondral layer or 1~3 according to the degree of depletion (loss of staining). Arthritis was considered to be present if the degree of depletion showed above 2, which is described in the literature (Lubberts Erik et al., *J. Immunol.*, 163, pp4546–4556, 1999).

A characteristic parameter in CIA is the progressive loss of articular cartilage. The destruction was graded separately on a scale of 0~3, ranging from fully stained cartilage to detained cartilage or complete loss of articular cartilage. Pannus formulation was scored arbitrarily as 0 when no pannus formed in the joint space or 1~2 according to the degree of pannus formation. All these evaluation procedures of histological analysis were performed in a blinded manner.

Arthritis progression in the ankle was evaluated by macroscopic symptoms such as joint swelling, and molecular biologic symptoms such as cytokine expression relating to cartilage destruction and protection.

Articular swelling was scored arbitrarily 0 when normal, 1 when slight swelling and rubber, 2 when remarkable swelling and rubber or 3 when edema accompanying wound according to the degree of macroscopic symptom with the determining standard described in the literature (Apparailly Florence et al., *J. Immunol.*, 160, pp5213–5220, 1998). Arthritis was considered to be present if the degree of macroscopic symptom was above 2.

Molecular biologic symptoms were evaluated by hematic amount of IL-4 which mainly works for cartilage protection, serum MMP-2 expression levels which is known to play a role in the cartilage depletion, and serum TIMP-2 (MMP's inhibitor) expression levels which is known to play a role in the inhibition of cartilage depletion. Expression levels were measured by using ELISA reader (VERSAmax, Molecular Devices, USA). Arthritis was considered to be present if the degree of MMP-2 was above 10 ng per 1 g of the articular protein.

Result

We confirmed that preventive and therapeutic effect of the complex herbal composition by using collagen-induced arthritis (CIA) model in mice for arthritic diseases is potent, and in particular, it is confirmed that the PG201-1 and PG201-2 in the present invention exhibit such potent anti-inflammatory and protective effect by using macroscopic, histological and molecular biologic views of rheumatic arthritis.

The increase of joint swelling was significantly reduced in the mice treated with PG201-1 and PG201-2 compared to the control mice. For example, the incidence of arthritis in the control mice was 55%, while PG201-1 and PG201-2 treating group were 15% and 25%, respectively. These data showed that administration of PG201-1 and PG201-2 in the present invention could suppress remarkably the incidence of arthritis (Table 2 and FIG. 3). We also confirmed that paw thickness and index grade of arthritis were reduced remarkably by administration of PG201-1 and PG201-2 (FIG. 4a and FIG. 4b).

Effects of PG201-1 and PG201-2 were also examined by histological evaluation in synovial tissues and fluids. Safranin O-staining of proteoglycan in the cartilages showed that the proteoglycan was well preserved in the joints treated with PG201-1 and PG201-2, but not in the joints treated with a control vehicle. We confirmed that the depletion of articular cartilage of knee joints was significantly reduced to 15% and 25% by administration PG201-1 and PG201-2, respectively, while the control shows 90% of the degree of cartilage depletion (FIGS. 5a, 5b, 5c, 5d, 5e and 5f).

Figure 6A:
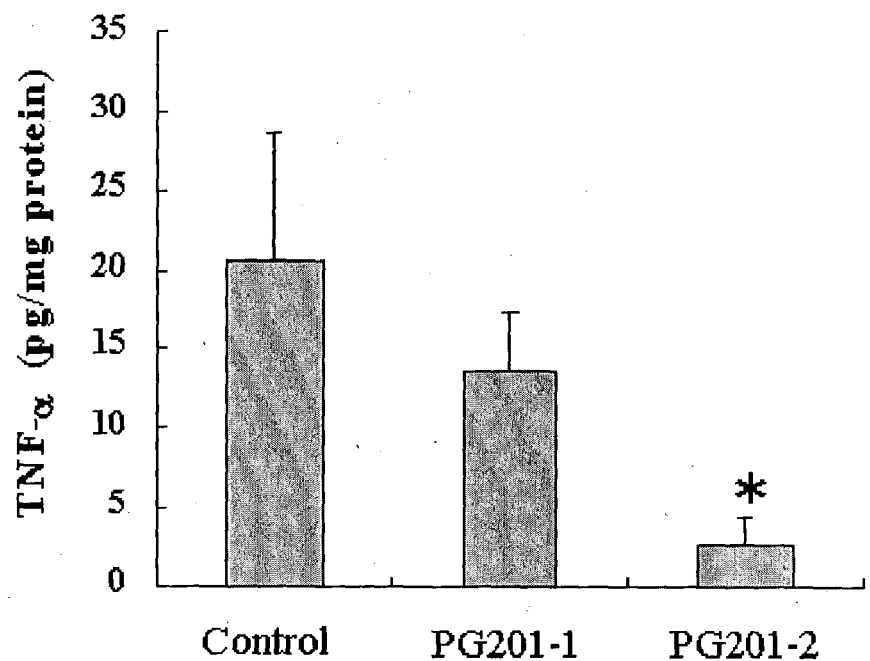
FIG. 6a presents inhibitory effect for TNF-α in ankle joint by administrating PG201-1 and PG201-2.
Figure 6B:
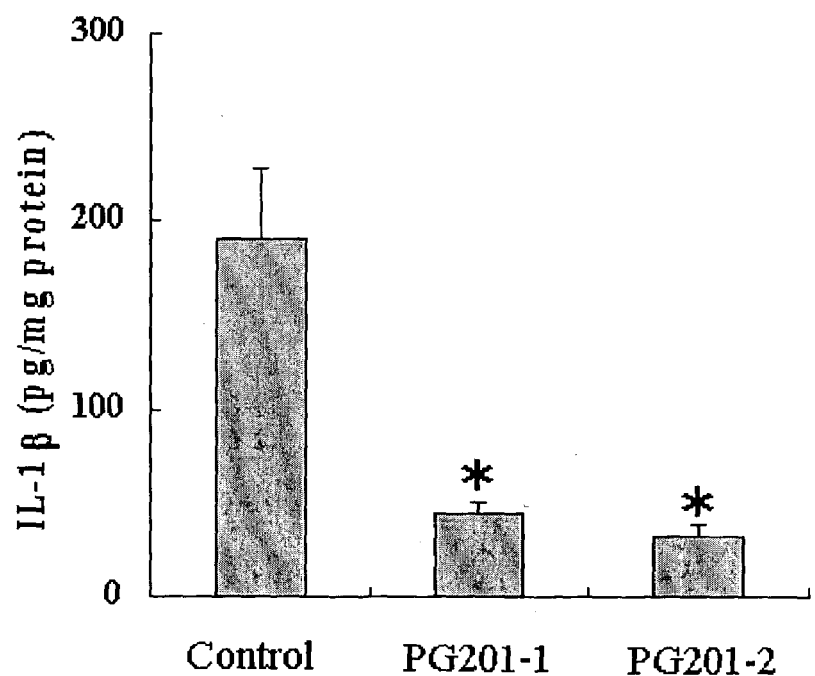
FIG. 6b shows inhibitory effect for IL-1β in ankle joint by administrating PG201-1 and PG201-2.
Figure 7:
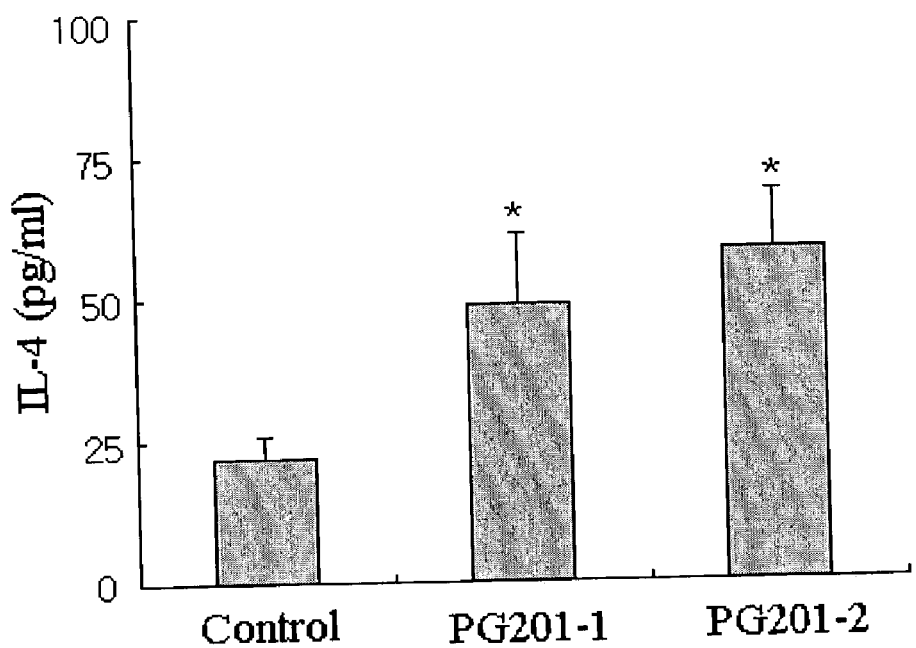
FIG. 7 presents activating effect of IL-4 relating to protection and keep of articular cartilage by administration PG201-1 and PG201-2.
Figure 8:
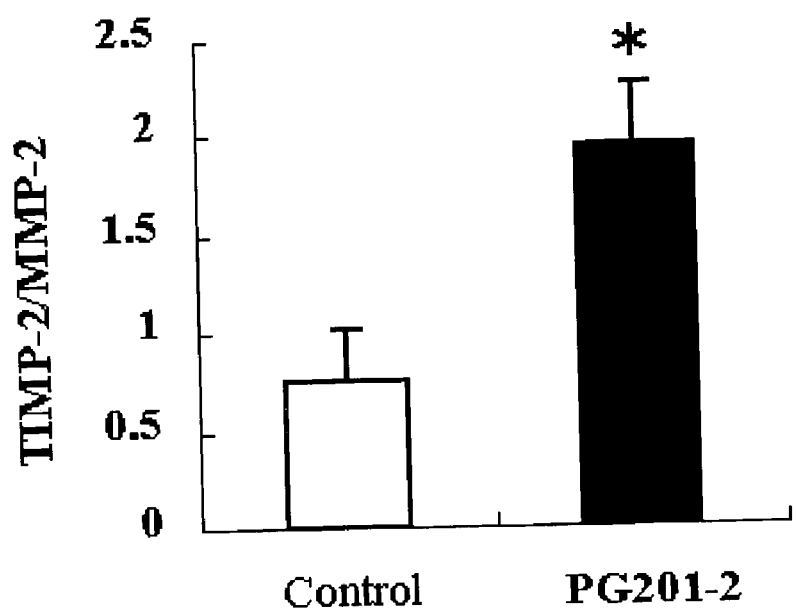
FIG. 8 depicts hematic relative ratio of cartilage destructor, MMP-2 (Matrix metalloproteinase-2), and cartilage protector, TIMP-2 (Tissue inhibitor of metalloproteinase-2) by administrating PG201-2.
Figure 9A:
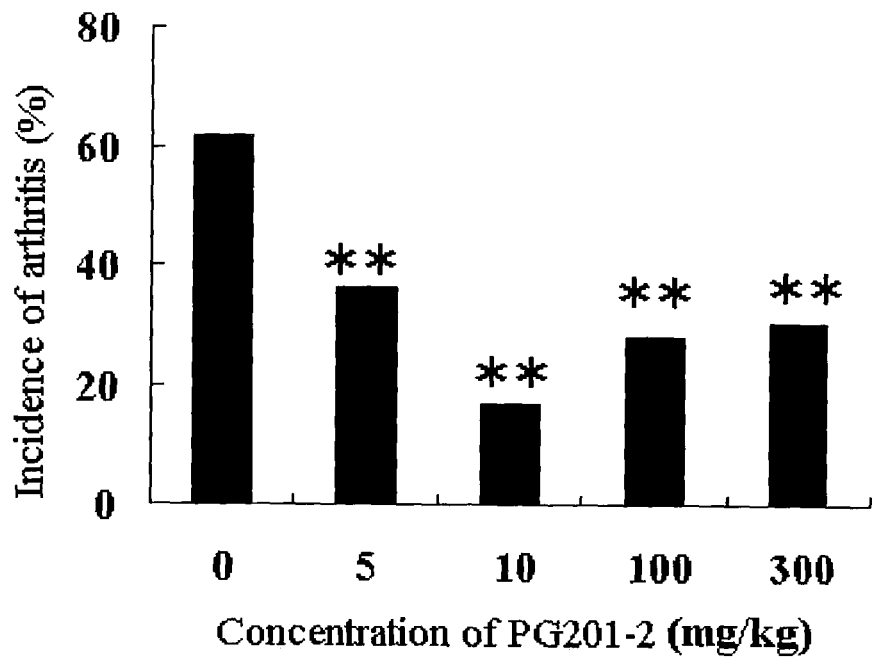
FIG. 9a presents dose response diagram of PG201-2 on incidence of arthritis.
Figure 9B:
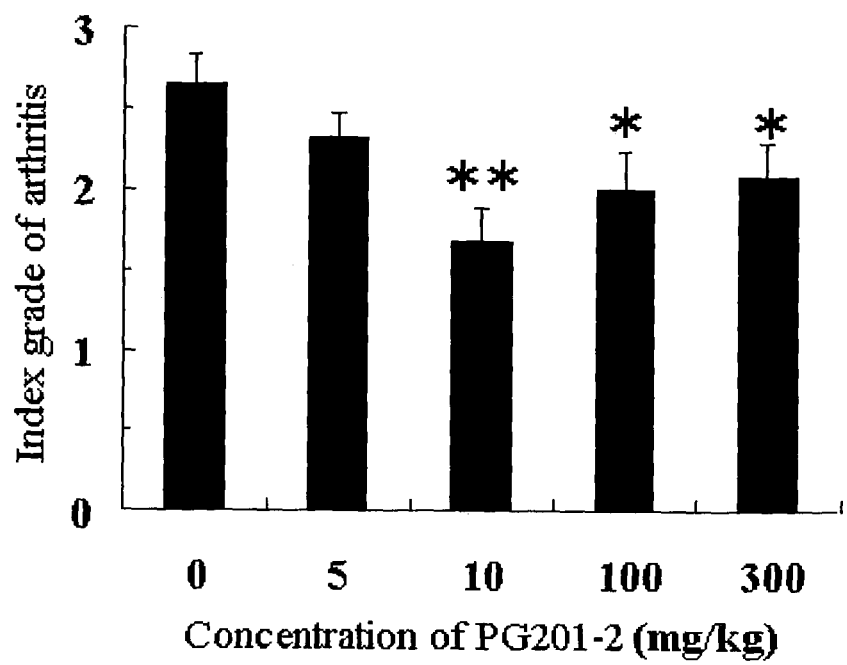
FIG. 9b presents dose response diagram of PG201-2 on index grade of arthritis.

Consistent with the joint swelling, a 50% of decrease in the level of pro-inflammatory cytokines, e.g., TNF-$\alpha$, IL-1$\beta$, by administration of PG201-1 and PG201-2 was observed as comparing with that of the control group (FIG. 6a and FIG. 6b). And we confirmed that IL-4 which works for protection and sustenance of articular cartilage was significantly increased twice by administration of PG201-1 and PG201-2 (FIG. 7). Also, it is confirmed that the PG201-2 in the present invention increase two times ratio of TIMP-2 to MMP-2 by measurement of hematic expression quantity of MMP-2 and its inhibitor, TIMP-2 (FIG. 8). Besides, above 20 mg/kg of PG201-2 exhibited such potent inflammatory and therapeutic effect for arthritic diseases, when PG201-2 ranging from 5 mg/kg to 300 mg/kg was tested (FIG. 9a and FIG. 9b).

The above mentioned results demonstrated that oral administration of the complex herbal composition in the present invention can remarkably reduce the incidence of arthritis in the knee joint and ankle joint induced arthritis, inhibit arthritis progression by in vitro regulation of cytokines relating to articular protection and damage, and protect articular cartilage. And the results suggest that the complex herbal composition has a therapeutic potential as an anti-inflammatory and anti-arthritic agent.

TABLE 2

| | Incidence of arthritis on item | | |
|---|---|---|---|
| | Joint swelling (%) | Cartilage depletion (%) | MMP-2 detection (%) |
| Control | 55 | 90 | 85 |
| PG201-1 | 15 | 38 | 46 |
| PG201-2 | 25 | 41 | 41 |

Experiment Example 2

Inhibition of Inflammatory Cytokines in Synovial Fibroblasts

In order to confirm the therapeutic effect of the PG201-1 and PG201-3 obtained in the Example 1 and Example 3 on arthritis, the experiment was performed as follows.

Method

Human subjects consisting of one normal subject, two subjects with rheumatic arthritis, and one subject with osteoarthritis who underwent the operation (synovectomy and arthroplasty), were studied. Their knee joints were dissected and their synovium were isolated by enzymatic degradation method described in the literature (Takaynagi H, et al., *Biochem. Biophys. Res. Commun.*, 240, pp279–286, 1997). The synovium was incubated for 90 minutes in the culture medium containing 1 mg/ml of collagenase (Boehringer-Mannheim, USA) and 0.15 mg/ml of DNAse I and filtered by 70 μm of cell strainer. The suspended cells were laid on Ficoll/Paque solution (Armersham Biosciences, Sweden), centrifuged for 30 minutes to obtain pure synovial fibroblasts and washed with saline. The separated cells were transferred to 20% (v/v) of FBS/DMEM (VERSAmax, Molecular devices, USA) medium, incubated at 37° C., 5% of $CO_2$ and 95% air. Each aliquot ($1\times10^5$) of the separated cells was transferred to 24 well plate, treated with 1 ng/ml of IL-1β for 1 hour, thereafter, treated with samples and incubated for 48 hours and then treated with 100 μg/ml of PG201-1 and PG201-3, 5 μg/ml of methotrexate, a anti-rheumatic agent, 100 μg/ml of glucosamine, stimulator of cartilage formulation. Each aliquot of the supernatants were collected after incubation for 48 hours and the amount of inflammatory cytokines such as IL-6 and IL-8 were determined by ELISA Reader (VERSAmax, Molecular devices, USA) (Inoue H, et al., *Acta. Pol. Pharm.*, 57, pp238–239, 2000: Shikham A. R., et al., *J. Immunol.*, 166, pp5155–5160, 2001).

Result

Figure 10:
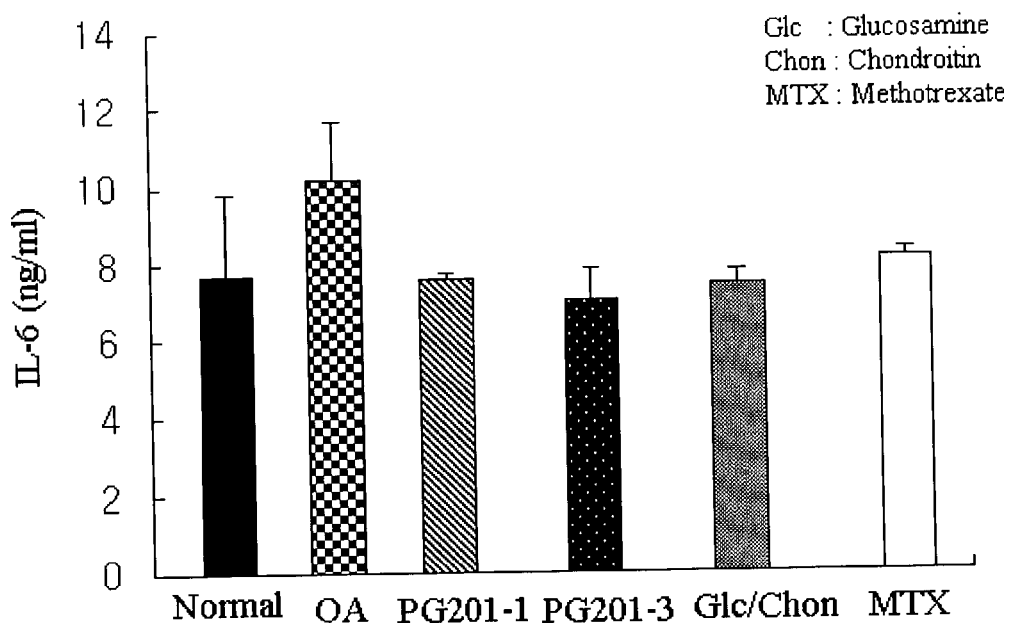
FIG. 10 represents inhibitory effect for IL-6 in synovial fibroblasts of osteoarthritis, by administrating PG201-1 and PG201-3.
Figure 11:
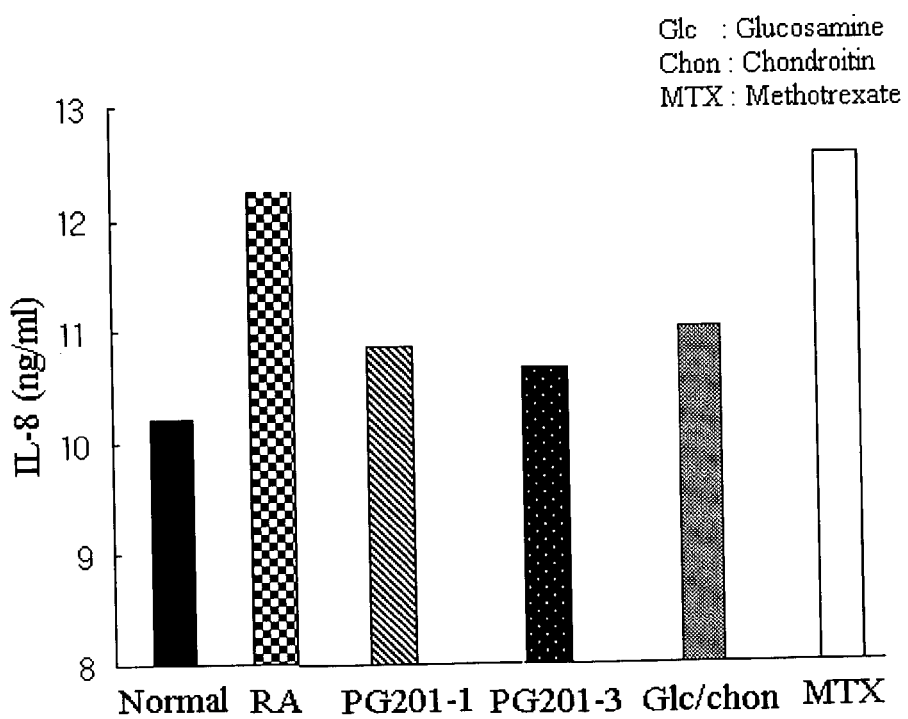
FIG. 11 shows inhibitory effect for IL-8 in synovial fibroblasts of rheumatic arthritis, by administrating PG201-1 and PG201-3.
Figure 12A:
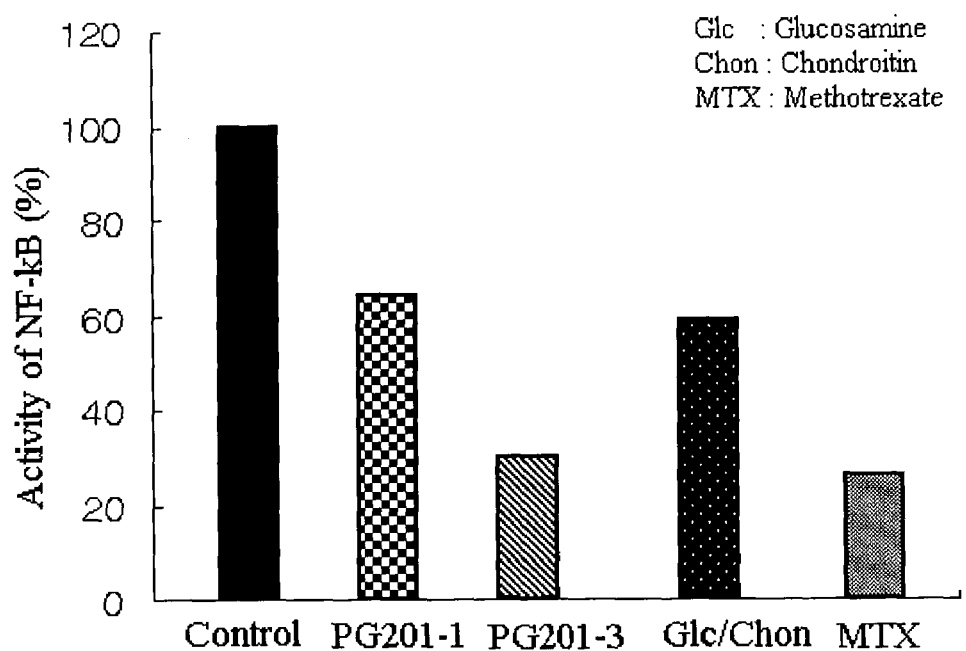
FIG. 12a shows inhibitory effect for NF-κB in normal kidney epithelium 293 cells by administrating PG201-1 and PG201-3.
Figure 12B:
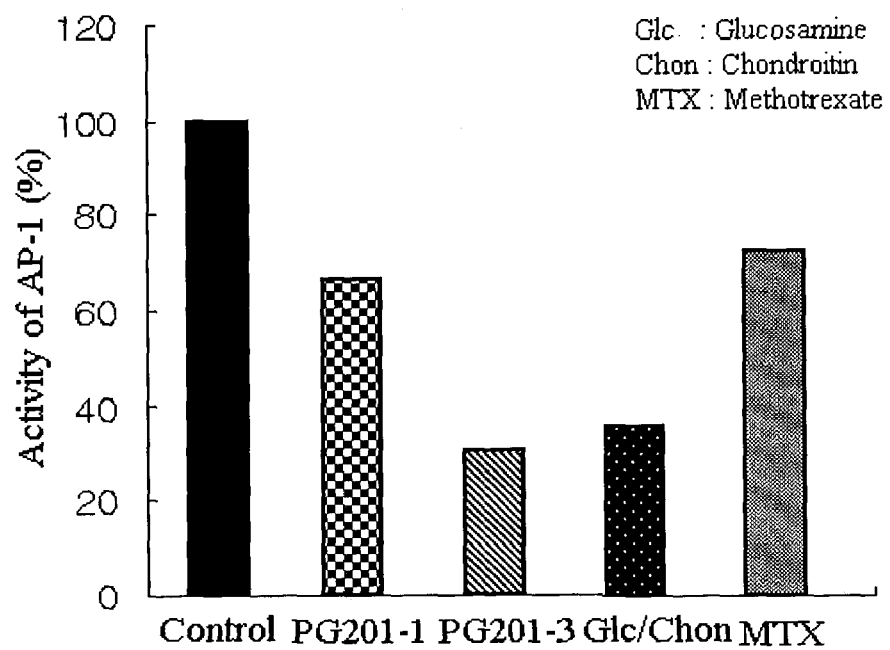
FIG. 12b presents inhibitory effect for AP-1 in normal kidney epithelium 293 cells by administrating PG201-1 and PG201-3.
Figure 12C:
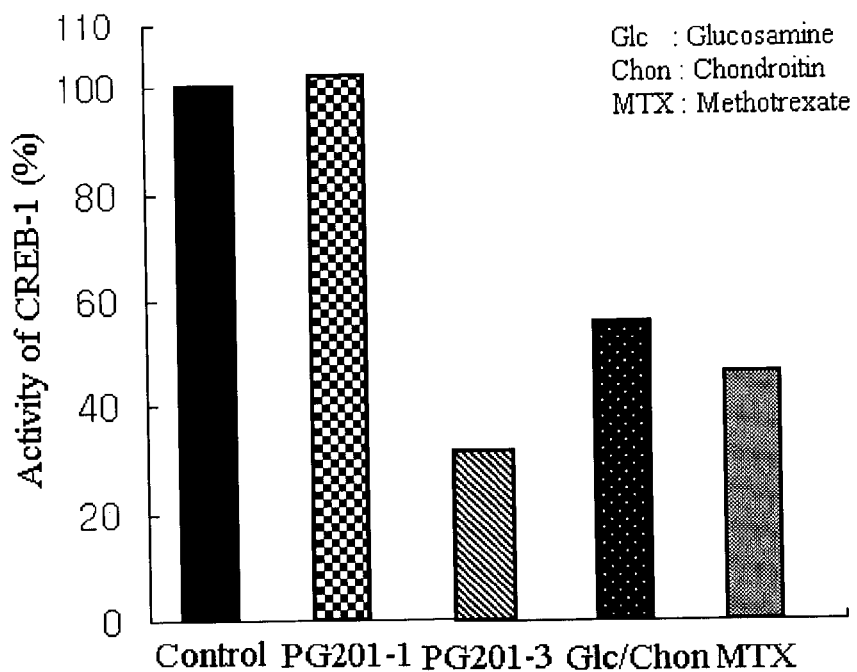
FIG. 12c present inhibitory effect for CREB-1 in normal kidney epithelium 293 cells by administrating PG201-1 and PG201-3.
Figure 12D:
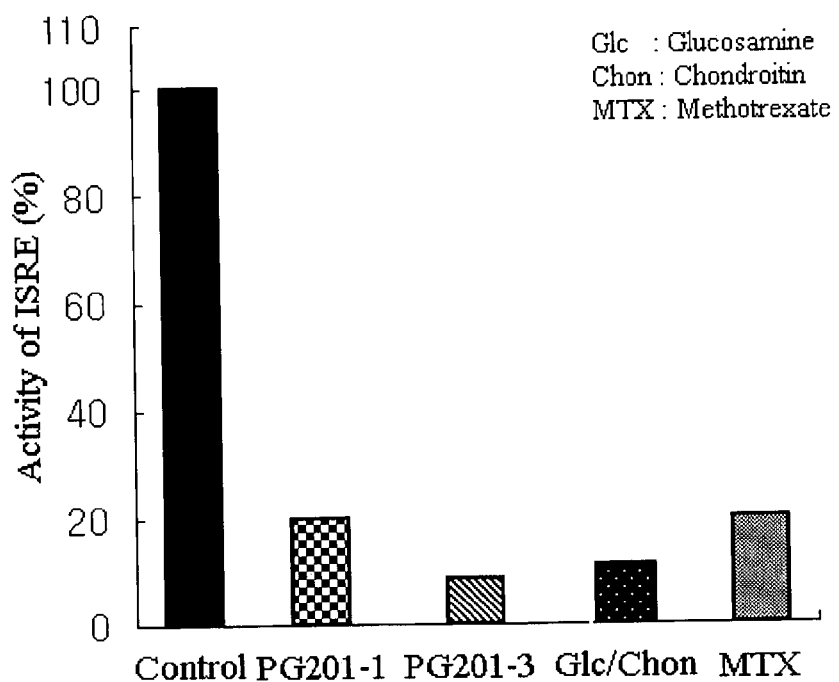
FIG. 12d shows inhibitory effect for ISRE in normal kidney epithelium 293 cell by administrating PG201-1 and PG201-3.

The results demonstrated that PG201-1 and PG201-3 in the present invention can inhibit in an equivalent or more effective manner than that of conventional anti-rheumatic drug, methotrexate (MTX) (FIG. 10 and FIG. 11). And the result suggests that the PG201-1 and PG201-3 have potential as an anti-inflammatory and anti-rheumatic agent.

Experiment Example 3

Inhibition and Regulation of Inflammatory Cytokines in Normal Kidney 293 Cell

In order to confirm the therapeutic effect of the PG201-1 and PG201-3 obtained in the Example 1 and Example 3 on arthritis, the experiment was performed as follows.

Method

Normal kidney epithelium 293 cells (ATCC, USA) were used. Each aliquot ($1\times10^5$) was transferred to 24 well plate, stabilized for 6 hours and transfected with DNA plasmid cloned luciferase reporter, containing NF-κB, AP-1, CREB-2 or ISRE and non-liposomal lipid formulation, effectene (QIAGEN, USA) (Maekawa k, et al., *Inflamm. Res.*, 48(11), pp575–581, 1999). After incubation for 24 hours, the medium was removed and the cells were treated with samples, incubated for 24 hours, collected, reacted with Luciferase reporter assay system (Promega, USA) and measured for activity of NF-κB, AP-1, CREB-2 and ISRE by using chemiluminometer (Victor1420, Wallac, USA). Concentration of PG201-1 and PG201-3 used in this experiment was the same in the above Experiment Example 2.

Result

The results demonstrated that PG201-1 and PG201-3 in the present invention can inhibit the activity of inflammatory cytokines, e.g., NF-κB, AP-1, CREB-2 or ISRE, relating to the progression of arthritis (FIG. 12a, FIG. 12b, FIG. 12c and FIG. 12d).

Experiment Example 4

Human Clinical Study for Arthritis

In order to confirm the therapeutic effect of the PG201-2 obtained in the Example 2 on various arthritic diseases, the experiment was performed as follows.

Method Seventy one adults, ranging from 23 to 82 years old suffering from various arthritic diseases were orally administered with PG201-2 for 1 to 6 months everyday according to their arthritic disease symptoms, and thereafter, the degree of relief/improvements in their arthritic disease symptoms were evaluated collectively by the alleviation of pains and the increase of joint mobility and the like.

Result

The results demonstrated that PG201-2 in the present invention has no side effect, and in particular, it is confirmed that the PG201-2 exhibit above 50% of therapeutic effect in osteoarthritis and rheumatic arthritis, and above 70% of therapeutic effect in patient suffering with various arthritis (Table 3).

TABLE 3

Human clinical study of PG201-2

| Symptom (N = 71) | Improvement | | | Hospital diagnosis |
|---|---|---|---|---|
| | Below 20% | 20~25% | Above 50% | |
| Osteoarthritis (Degenerative arthritis) N = 17 | 6 (35.3%) | 4 (23.5%) | 7 (41.2%) | ○ |
| Rheumatic arthritis N = 4 | 2 (50.0%) | | 2 (50.0%) | ○ |
| Lumbago, disc, ischialgia N = 13 | 1 (7.7%) | 4 (30.8%) | 8 (61.5%) | ○ |
| General arthritis (knee, wrinkle, waist, shoulder) N = 37 | 4 (10.8%) | 2 (5.4%) | 31 (83.8%) | X |

Experiment Example 5

Toxicity Test

In order to examine the cytotoxicity of PG201-2 obtained in the Example 2, the experiment was performed as follows.

Methods

The acute toxicity on SPF Sprague-Dawley rats (Biogenomics), having its mean body weight of 108.3~126.0, was performed using PG201-2. Each group consisting of 5 rats was administrated orally with 8000 mg/kg of PG201-2 and observed for 14 days. This test was carried out in compliance with the Testing Guidelines for Safety Evaluation of Drugs (Notification No. 1999-61) issued by Korea Food and Drug Administration and the Good Laboratory Practice Regulations for Non-clinical Laboratory Studies (Notification No. 2000-63) issued by Korea Food and Drug Administration and OECD Principles of Good Laboratory Practice.

Results

There were no treatment-related effects on mortality, clinical signs, body weight changes and gross findings in any group or either gender by using 8000 mg/kg of PG201. These results suggested that the compounds prepared in the present invention were potent and safe.

Hereinafter, the formulating methods and kinds of excipients will be described, but the present invention is not limited to them. The representative preparation examples were described as follows.

| Preparation of injection | |
|---|---|
| PG201-1 | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 ml ample and sterilizing by conventional injection preparation method.

| Preparation of powder | |
|---|---|
| PG201-2 | 500 mg |
| Corn Starch | 100 mg |
| Lactose | 100 mg |
| Talc | 10 mg |

Powder preparation was prepared by mixing above components and filling sealed package.

| Preparation of tablet | |
|---|---|
| PG201-2 | 200 mg |
| Corn Starch | 100 mg |
| Lactose | 100 mg |
| Magnesium stearate | optimum amount |

Tablet preparation was prepared by mixing above components and entabletting.

| Preparation of capsule | |
|---|---|
| PG201-3 | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

| Preparation of liquid | |
|---|---|
| PG201-3 | 1000 mg |
| Sugar | 20 g |
| Polysaccharide | 20 g |
| Lemon flavor | 20 g |

Liquid preparation was prepared by dissolving active component, and then filling all the components in 1000 ml ample and sterilizing by conventional liquid preparation method.

| Preparation of health food | |
|---|---|
| PG201-2 | 1000 mg |
| Vitamin mixture | optimum amount |
| Vitamin A acetate | 70 µg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 µg |
| Vitamin C | 10 mg |
| Biotin | 10 µg |
| Amide nicotinic acid | 1.7 mg |
| Folic acid | 50 µg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

| Preparation of health beverage | |
|---|---|
| PG201-1 | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A pharmaceutical composition comprising a herbal extract as the active ingredient, including, in combination: *Chaenomelis Fructus, Achyranthis Radix, Acanthopanax*

*Cortex, Phlomidis Radix, Gentianae Radix, Clematidis Radix, Angelica Radix, Cnidii Rhizoma, Gastrodiae Rhizoma, Safflower, Cinnamomi Cortex,* and *Ledebouriellae Radix,* and a pharmaceutically acceptable carrier for treating arthritic diseases.

2. The pharmaceutical composition according to claim 1, wherein the components of the active ingredient including *Chaenomelis Fructus, Achyranthis Radix, Acanthopanax, Phlomidis Radix, Gentianae Radix* and *Clematidis Radix* are in a ratio of 1:0.5~2:0.5~2:0.5~2:0.5~2:0.5~2.

3. The pharmaceutical composition according to claim 1, wherein said arthritic diseases comprise: acute arthritis, chronic rheumatoid arthritis, arthritis deformans, or degenerative arthritis.

4. The pharmaceutical composition according to claim 1, wherein said composition contains about 0.01 to 95 w/w % of the extract based on the total weight of the composition.

5. The pharmaceutical composition according to claim 1, wherein said pharmaceutical composition is provided in an acceptable carrier as powder, granule, tablet, capsule, aqueous medicine or injection.

* * * * *